United States Patent [19]
Drysdale et al.

[11] Patent Number: 5,236,560
[45] Date of Patent: Aug. 17, 1993

[54] SOLVENTLESS DIMERIC CYCLIC ESTER DISTILLATION PROCESS

[75] Inventors: Neville E. Drysdale; Thomas W. Stambaugh, both of Newark; James V. Tarbell, Hockessin, all of Del.

[73] Assignee: E. I. du Pont de Nemours and Company, Wilmington, Del.

[21] Appl. No.: 813,189

[22] Filed: Mar. 13, 1992

[51] Int. Cl.$^5$ ................ B01D 3/00; C07D 319/10
[52] U.S. Cl. ................ 203/99; 203/DIG. 19; 203/DIG. 21; 549/274
[58] Field of Search ................ 203/91, DIG. 11, 99, 203/DIG. 19, DIG. 21; 549/274; 562/589

[56] References Cited

U.S. PATENT DOCUMENTS

| | | | |
|---|---|---|---|
| 1,095,205 | 5/1914 | Gruter et al. | |
| 2,668,162 | 2/1954 | Lowe | 260/78 |
| 4,797,468 | 1/1989 | De Vries | 528/354 |
| 4,835,293 | 5/1989 | Bhatia | 549/274 |
| 4,966,982 | 10/1990 | Ono et al. | 549/274 |
| 4,983,745 | 1/1991 | Muller et al. | 549/274 |
| 4,990,222 | 2/1991 | Aigner et al. | 549/274 |
| 5,023,349 | 6/1991 | Bhatia | 549/274 |
| 5,043,458 | 8/1991 | Bhatia | 549/274 |
| 5,053,522 | 10/1991 | Muller | 549/274 |
| 5,089,632 | 2/1992 | Paul | 549/274 |
| 5,117,008 | 5/1992 | Bhatia et al. | 549/274 |

FOREIGN PATENT DOCUMENTS 1108720  4/1968  United Kingdom ............ 549/274

Primary Examiner—Virginia Manoharan
Attorney, Agent, or Firm—Don O. Winslow

[57] ABSTRACT

A dimeric cyclic ester of an alpha-hydroxycarboxylic acid (lactide) is separated and recovered from a vapor product stream containing the cyclic ester, the corresponding lower-boiling hydroxycarboxylic acid (lactic), higher-boiling oligomeric hydroxycarboxylic acid and water without the use of solvents. More specifically, the vapor stream is condensed to obtain a condensate containing substantially all the cyclic ester, and the condensate is refined by distillation means alone to recover the cyclic ester substantially free of water, the alpha-hydroxycarboxylic acid and the higher-boiling oligomers.

7 Claims, 2 Drawing Sheets

SOLVENTLESS DIMERIC CYCLIC ESTER DISTILLATION PROCESS

BACKGROUND OF THE INVENTION

1. Field of the Invention

This invention relates to an improved process for the separation and recovery of a dimeric cyclic ester of an alpha-hydroxycarboxylic acid from vapor product streams comprising the cyclic ester and hydroxylic impurities including the alpha-hydroxycarboxylic acid. More particularly, the invention relates to a solventless distillation process for said separation and recovery. Still more particularly, the invention relates to such a solventless process wherein the vapor product stream is produced on depolymerizing an oligomer of an alpha-hydroxycarboxylic acid, the vapor product stream is condensed and fractionally distilled to recover the cyclic ester.

2. Description of Related Art

Dimeric cyclic esters of hydroxycarboxylic acids such as glycoide (1,4-dioxane-2,5-dione) and lactide (1,4-dioxane-3,6-dimethyl-2,5-dione), are intermediates to high molecular weight polyhydroxycarboxylic acids which may be useful in biomedical and other applications because of their ability to be degraded biologically and hydrolytically to form physiologically and environmentally acceptable by-products.

To achieve the high molecular weights required for such use it is necessary the cyclic ester be substantially free of hydroxylic (including hydroxycarboxylic) impurities, since such impurities prevent the attainment of the desired molecular weights. It is preferred the acid content of lactide, for example, be less than 10 milliequivalents per kilogram (meq/kg), more preferably less than 5 meq/kg.

Lactide and other dimeric cyclic esters of alpha-hydroxycarboxylic acids are most conveniently prepared by polymerizing the corresponding alpha-hydroxyacid to a relatively low molecular weight (oligomeric) polyhydroxycarboxylic acid, then heating the oligomer, generally in the presence of a catalyst, as is well known in the art, to depolymerize it to the cyclic ester (lactide) which is recovered as a component of a vapor product stream, see for example, Gruter et al., U.S. Pat. No. 1,095,205 (1914); Lowe, U.S. Pat. No. 2,668,162 (1954); Bhatia, U.S. Pat. No. 4,835,293 (1989); DeVries, U.S. Pat. No. 4,797,468 (1989); and Muller U.S. Pat. No. 5,053,522 (1991).

The vapor product stream invariably contains not only the dimeric cyclic ester but volatile hydroxylic impurities, among them water, the monomeric alpha-hydroxyacid, which is generally more volatile than the dimeric ester, and often higher boiling oligomers of the alpha-hydroxyacid, all of them undesirable as they are polymerization chain stoppers.

Further, under the conditions of typical previously known art procedures for the separation and recovery of the cyclic ester from the vapor product stream, such as condensation, scrubbing with a solvent or crystallization from a solvent, the hydroxylic impurities, particularly water and alpha-hydroxycarboxylic acid, are capable of undergoing ring-opening reactions with the cyclic ester, resulting in decrease in cyclic ester yield and increase in the acidity of the cyclic ester product. Such reactions are more prone to occur the higher temperature of the recovery process employed.

For example, removal and recovery of a cyclic ester such as lactide from the vapor product stream by scrubbing with an alcohol such as isopropyl alcohol, as exemplified in U.S. Pat. Nos. 4,835,293 and 5,053,522, not only provides a medium for potential yield-decreasing reaction of the vapor stream hydroxylic impurities with the lactide product but entails the further possibility of the hydroxylic solvent itself reacting with the cyclic ester to form yield-decreasing open-chain derivatives thereof.

Moreover, reliance on a solvent, whether for scrubbing the vapor product stream to recover the cyclic ester or for purifying it by recrystallization, is disadvantageous as it necessitates facilities for storing the solvent, using it, purifying it and preventing it from escaping into and contaminating the environment, all of which adds significantly to the process investment and operating costs.

SUMMARY OF THE INVENTION

In view of the above problems associated with the previously known process, it is an object of this invention to provide a process for the separation and recovery of dimeric cyclic esters from vapor product streams containing hydroxylic impurities that effects the separation of the ester from the impurities without the use of a solvent.

It is another object to provide such a separation and recovery process that relies on relative volatilities to effect separation of the cyclic ester from the corresponding and lower-boiling monomeric alpha-hydroxycarboxylic acid, the higher-boiling oligomeric hydroxycarboxylic acids and water when present.

Still another object is to provide a solvent-less process which enables the separation and recovery of lactide and other dimeric cyclic esters from vapor product streams by distillation means alone.

Thus the present invention provides a process for the separation and recovery of a dimeric cyclic ester from a vapor product stream containing said ester and minor amounts of one or more hydroxylic impurities including an alpha-hydroxycarboxylic acid more volatile than the cyclic ester and optionally including water and oligomeric hydroxycarboxylic acid higher-boiling (i.e., less volatile) than the cyclic ester, which process comprises condensing the vapor stream and fractionally distilling the condensate to separate the cyclic ester from residual hydroxylic impurities, including lower-boiling monomeric alpha-hydroxycarboxylic and, when present, higher-boiling oligomeric hydroxycarboxylic acids, and recovering a dimeric cyclic ester fraction having a substantially lowered acid content.

Preferably, the cyclic ester is a lactide, which may be L-, D-m, meso- or racemic lactide, and the alpha-hydroxycarboxylic acid is L-, D- or racemic lactic acid, and the higher-boiling acid impurity is an oligomer of a lactic acid as above.

By "hydroxylic impurities" as used herein it is meant to include hydroxycarboxylic acids such as the monomeric alpha-hydroxy acid and low molecular weight oligomeric hydroxycarboxylic acids thereof as well as water, which is normally produced therewith as volatile impurities in the vapor product stream formed on depolymerizing/thermolyzing an oligomer of an alpha-hydroxycarboxylic acid such as lactic acid.

The invention is based on the discovery that impure cyclic ester as defined can be separated from its impurities and obtained thereby as polymer grade material by distillation means alone, more particularly by fractional distillation at temperatures and pressures that minimize acid-producing side reactions. The solventless distillation process of this invention is surprisingly effective and economic for the intended purpose in view of the dynamic nature of the water-hydroxycarboxylic acid(s)-cyclic ester system and its propensity to deteriorate in terms of cyclic ester quality under conditions of thermal stress.

DESCRIPTION OF THE PREFERRED EMBODIMENTS

Figure 1:
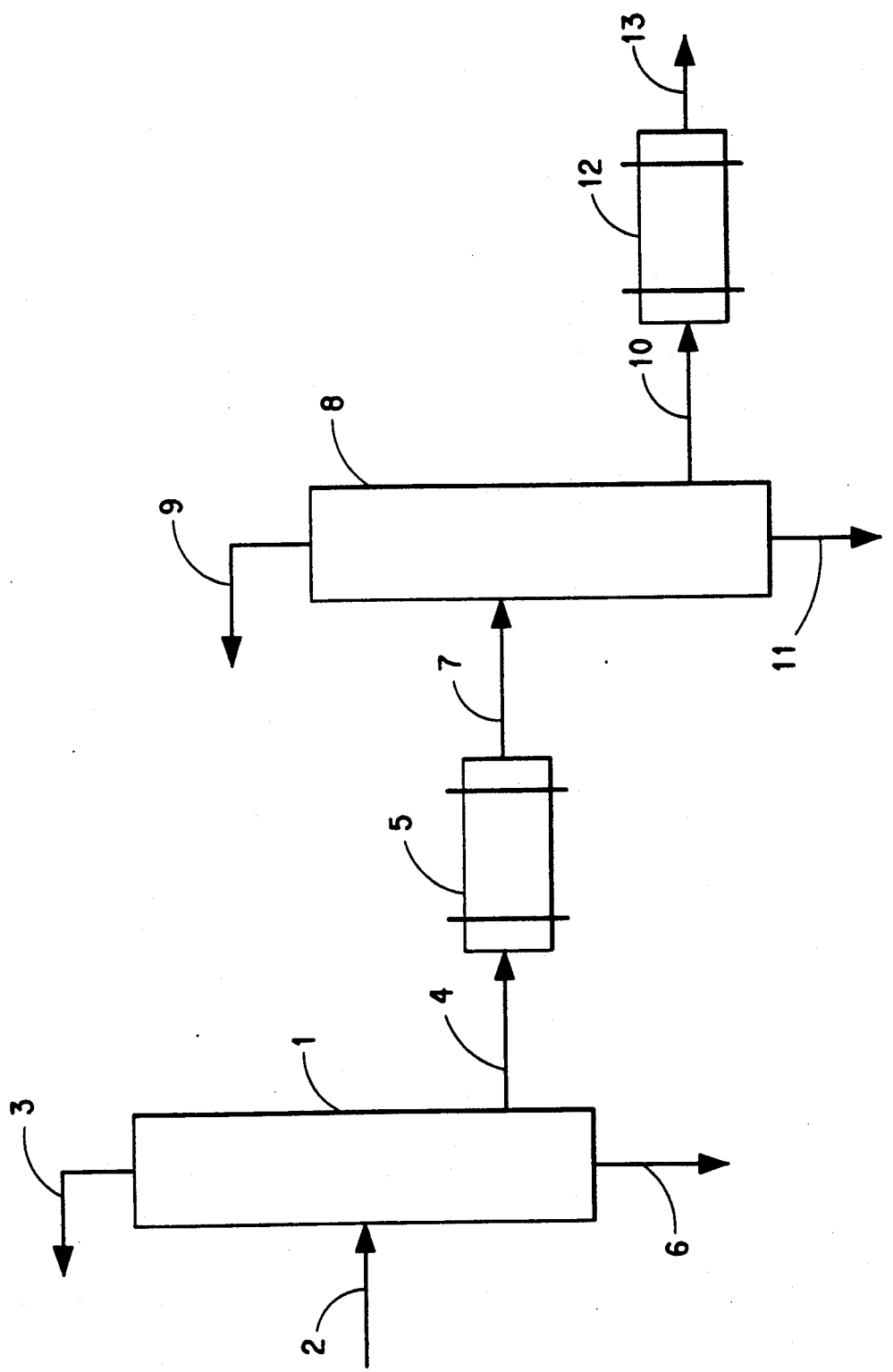
FIG. 1 is a schematic representation of a fractional distillation system comprising two distillation columns and two heat exchangers (condensers).

The invention is applicable to the separation and recovery of dimeric cyclic esters of alpha-hydroxycarboxylic acids from vapor streams containing the cyclic ester and minor proportions of the alpha-hydroxycarboxylic acid. It is also applicable to such compositions optionally containing minor proportions of water and low molecular weight oligomers of the alpha-hydroxycarboxylic acids. It is particularly applicable to the recovery of the dimeric cyclic esters from vapor product streams produced by depolymerizing a depolymerizable oligomer of an alpha-hydroxycarboxylic acid at elevated temperatures. Included are such processes conducted at reduced pressures as disclosed for example in Gruter et al., U.S. Pat. No. 1,095,205 and Muller, U.S. Pat. No. 5,053,522, which patents are hereby incorporated herein by reference. Also included as such depolymerization processes conducted at substantially atmospheric pressure wherein a carrier gas is employed to sweep the cyclic ester and other volatile components out of the depolymerization reaction mass, as disclosed in Bhatia, U.S. Pat. Nos. 4,835,293, 5,023,349 and 5,043,548, which patents are also incorporated herein by reference.

Thus, it will be appreciated the invention further refers to a process for the manufacture, recovery and purification, of a dimeric cyclic ester which comprises the steps of (a) oligomerizing an oligomerizable alpha-hydroxycarboxylic acid to a depolymerizable oligomer thereof, (b) subjecting the oligomer to depolymerizing conditions, usually in the presence of a catalyst, thereby producing a vapor product stream containing the corresponding cyclic ester and minor amounts of decomposition products normally including water, monomeric alpha-hydroxycarboxylic acid and one or more volatile higher-boiling oligomeric hydroxycarboxylic acids, and (c) processing the vapor product stream as defined above and more fully described hereinafter.

In general, the invention is applicable to the preparation, recovery and purification of cyclic esters having the formula

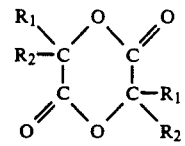

wherein $R_1$ and $R_2$ are independently hydrogen or an alkyl radical having 1 to 6 carbon atoms. Preferably $R_1$ and $R_2$ are H or methyl, as in glycolide (wherein $R_1=R_2=H$) and more preferably as in lactide (wherein $R_1=H$, $R_2=$methyl).

In general, it has been found the relative order of decreasing volatility of the principal components of a depolymerization vapor product stream (excluding carrier gas when such is used to strip the depolymerization products from the reaction mass) is water, monomeric alpha-hydroxycarboxylic acid (lactic acid), dimeric cyclic ester (lactide) and volatile oligomers of the alpha-hydroxy acid. For example, the boiling points of water, lactic acid (LA), lactide (LD) and lactoyllactic acid ($L_2A$) at atmospheric pressure at 100, 217, 259 (estimated) and 359° C. (estimated), respectively. The same relative order of volatility holds over a wide range of reduced pressures, although the ratio (or "alpha") of the vapor pressures exerted by any two components at a given temperature may change with change in pressure. The vapor pressures of each component over a range of temperatures are readily determined by trial and the "alphas" of the various component pairs are straightforwardly calculated. It is preferred to operate the fractional distillation process at coordinated temperatures and pressures such that the "alpha" of the alpha-hydroxyacid (lactic) vapor pressure to the cyclic ester (lactide) vapor pressure and the "alpha" of the cyclic ester vapor pressure to the $H(OCR_1,R_2CO)_2OH$ (lactoyllactic acid) vapor pressure are as high as practicable, preferably each "alpha" is at least about 5 at a particular condensation temperature and pressure.

Since the "alpha" ratio for any given pair of components tends to decrease with increasing temperature it is best to operate at low temperatures and pressures so as to maximize the degree of the separations desired.

In another aspect of the invention, the vapor product stream issuing from a depolymerization reactor, which contains the major proportion of a dimeric cyclic ester as defined (lactide) and minor amounts of one or more hydroxylic impurities including an alpha-hydroxycarboxylic acid more volatile than the cyclic ester and optionally water and oligomeric hydroxycarboxylic acid higher-boiling than the cyclic ester, can first be subjected to a partial condensation step to remove water and some of the volatile acid overhead and thereby provide a more concentrated cyclic ester fraction. The partial condensation step comprises: (a) passing the vapor stream into a partial condensation zone maintained at a temperature and pressure effective (i) to maintain at least a portion of the alpha-hydroxycarboxylic acid and substantially all the water when present in the vapor state and (ii) to form a condensate, preferably liquid, comprising substantially all the dimeric cyclic ester and a reduced concentration of alpha-hydroxycarboxylic acid; (b) removing the vapor fraction containing alpha-hydroxycarboxylic acid and little or no cyclic ester; and (c) recovering the condensate having substantially no water and a substantially reduced content of the alpha-hydroxyacid from the partial condensation zone. The condensate is then fractionally distilled for further purification in accordance with the method of this invention.

It is preferred to operate the partial condensation step at temperatures at which the condensed phase is liquid so as to facilitate the transfer of the condensate to the distillation step for the further refining of the condensed dimeric cyclic ester, Such operating (partial condensation) temperatures varies with the constitution of the dimeric cyclic ester; for lactide processing in accordance with this invention it is preferably at least about 100° C. Representative temperatures and pressures for the separation and recovery of lactide from a vapor product stream also containing water, lactic acid and higher-boiling oligomeric lactic acids are 100° C. at 2 mm Hg, 132° C. at 10 mm Hg, and 160° C. at 50 mm Hg. Similar relationships will be readily apparent to one skilled in the art from a consideration of the vapor pressure-temperature relationships for other dimeric cyclic esters, their corresponding alpha-hydroxycarboxylic acids, the oligomers thereof and water.

The vapor fraction exiting the partial condensation zone and consisting essentially of the hydroxycarboxylic acid, water (if present in the vapor product stream fed to the partial condensation zone) and small proportion of the cyclic ester can be further processed if desired to retrieve its cyclic ester content and the residual acid recycled to the oligomerization step.

The fractional distillation of the condensate from the partial condensation step can be conducted batchwise, but is best done continuously in a multi-stage column wherein (a) the condensate is fed to a mid-point of the column, (b) an overhead is established consisting essentially of volatile acid, residual water if any and some cyclic ester, which overhead is continuously taken off, (c) a cyclic ester fraction substantially free of water, lower-boiling acid and high-boiling acid is established and continuously taken off as a vapor sidestream at a point which is below the overhead takeoff and below the condensate feed point to the column, and (d) a highest boiling fraction consisting largely of oligomeric acid(s) and some cyclic ester is present at the bottom of the column, which is purged as necessary to maintain a balanced column. The feed rate of the condensate to the column and the take-off rates of the overhead, the cyclic ester fraction and the purge (heel) from the bottom-most fraction are coordinated such that a substantially steady state condition can be maintained in the column. Further, the overhead can be continuously processed to isolate a cyclic ester-rich component which can be recycled to the fractionating column and the acid-rich remainder recycled to the oligomerization step. Similarly, the purge (heel) taken from the bottom of the column, which is rich in oligomeric acids and contains some cyclic ester can be recycled to the depolymerization step for conversion to additional quantities of cyclic ester.

In the fractional distillation step, best results are achieved at low temperatures and pressures. Low temperatures minimize the possible occurrence of side reactions between water and/or acid with the cyclic ester that can lead to product loss and deterioration of product quality. For lactide recovery it is preferred the temperature be not greater than 220° C., more preferably not greater than 200° C., and most preferably not greater than 180° C.

For example, with reference to FIG. 1, crude lactide condensate containing lactic acid, optionally water and higher-boiling oligomers thereof obtained by condensing the vapor product stream issuing from a depolymerization unit is fed through line 2 to distillation column 1 maintained at a bottoms temperature not great than 180° C. and a pressure of 30 mm Hg, which conditions of temperature and pressure are sufficient to vaporize the feed material substantially completely.

A water and lactic acid vapor fraction containing some lactide is taken overhead via line 3, a lactide-rich fraction, largely free of water, lactic acid and higher-boiling oligomeric lactic acids is removed from the column as a vapor side stream through line 4 and is condensed to liquid in condenser 5 maintained at a temperature (about 100° C.) just above the melting point of the lactide.

A higher boiling bottoms stream consisting largely of oligomers and lactide is removed via line 6. The molten lactide condensed in 5 can be further refined, if desired, to provide still lower-acid content material by feeding the condensate from 5 through line 7 to a second fractionating column 8 also maintained at a bottom 180° C. and 30 mm Hg. The vapor overhead from 8 is removed through 9 the refined lactide vapor stream through 11 and the high-boilers through 12. The lactide vapor stream passes through condenser 13 where it is liquefied and advantageously emerges as a polymer-grade molten stream via exit line 14. This stream, if desired, can be fed directly in the molten state to a polymerizer for the production of high molecular weight polylactic acid. Should the molten stream exiting 14 perchance have a higher acid content than desired, it can be fed to a third fractionating column and the distillative refining process repeated.

The overhead stream exiting line 3, which is rich in water and lactic acid and may contain lactide can be dehydrated if necessary and fed to an oligomerization reactor (not shown) for conversion to a depolymerizable lactic acid oligomer as is known in the art.

Figure 2:
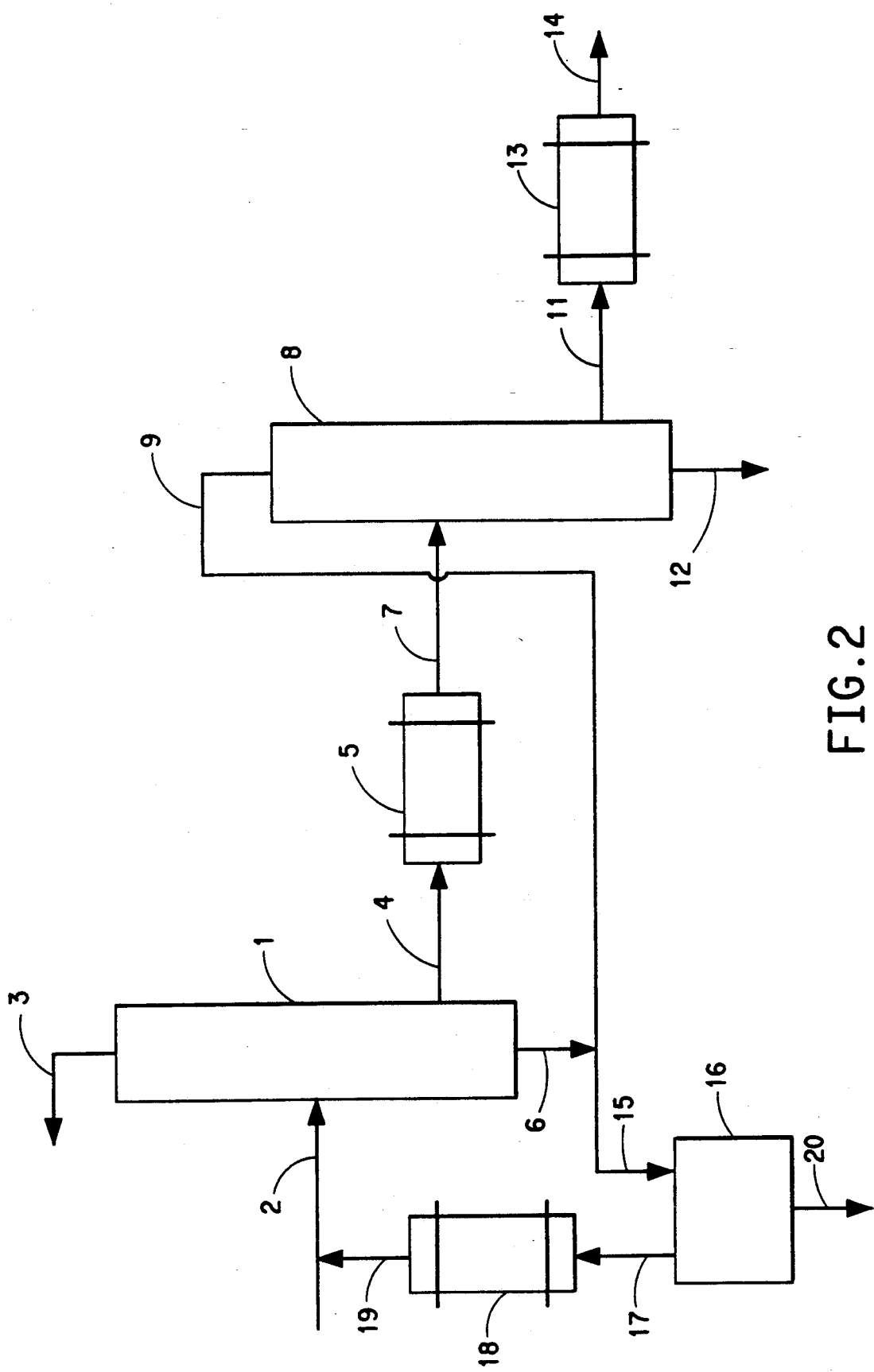
FIG. 2 is a schematic representation of an integrated fractional distillation system comprising the columns and condensers of FIG. 1 in conjunction with a third distillation zone in association with a third condenser and means for recycling the various vapor and liquid streams along the process loop.

Referring to FIG. 2, overhead lactide stream 9 containing lactic acid is combined with bottoms stream 6, both containing lactide and higher-boiling oligomers. The combined 6 and 9 stream is passed via line 15 to flash still 16, maintained at 125° C. and 10 mm Hg, from which is flashed residual lactic acid and the bulk of the lactide content of the combined stream as a vapor stream. The vapor stream exits 16 via line 17, passes through condenser 18, emerges as crude liquid lactide via line 19 composition and joins incoming crude lactide condensate from a depolymerization reactor (not shown) at line 2.

High-boiling oligomeric residue is removed from 16 through line 20. Its lactic acid values can be recovered, if desired, by hydrolysis; the hydrolysate can be concentrated and the concentrate fed to an oligomerization reactor (not shown) for conversion to a depolymerizable lactic acid oligomer as described above for the aqueous lactide stream exiting line 3.

The following examples are presented to further illustrate specific embodiments of the present invention and as such are not to be interpreted as being unduly limiting. Temperatures are in degrees Celsius and percentages in percent by weight unless otherwise stated.

EXAMPLE 1

This Example illustrates the cracking/depolymerization of an oligomer of L-lactic acid to form an impure L-lactide vapor stream and partial condensation of the vapor stream to obtain a high lactide content condensate, followed by fractional distillation of the condensate to recover low acid content L-lactide.

An oligomer of L-lactic acid was prepared by heating 88% L-lactic acid containing 0.3 percent stannous octoate at temperatures up to 180° with removal of water until the product had a degree of polymerization of about 10. The still molten (150°) oligomer was continuously cracked by feeding it to the top of a 7.62 cm diameter 5-sieve tray glass Oldershaw column heated to 210° and maintained at a reduced pressure of 10 mm Hg.

About 1,437 gms of the oligomer was fed to the cracking column over a 2.5 hour period, during which time about 71% of the oligomer was cracked to vaporized products. Partial condensation of the vapor product stream at 132° and 10 mm Hg pressure gave an acid-rich vapor (about 172 gms) and 843 grams of lactide-rich condensate containing 300 meg/kg of acidity corresponding to 253 meg of acidity. The condensate was immediately solidified by cooling at −10° for overnight storage.

The 843 gms of frozen condensate was liquefied by microwave heating and then batch-distilled in a 5.1 cm diameter 20 plate Oldershaw column at 5 mm Hg, a 4:1 to 6:1 reflux ratio, a bottoms temperature of 155°–157°, and a head temperature of 119°–124° over a 2.5 hour period. Five overhead cuts were taken as follows:

| Cut | Weight | Acidity |
|---|---|---|
| 1 | 66.1 gms | 674.8 meg/kg |
| 2 | 60.1 | 240 |
| 3 | 85.1 | 69 |
| 4 | 74.6 | 27.4 |
| 5 | 174.7 | 7.4 |
| Heel | 278.4 | 559 |

EXAMPLE 2

The procedure of Example 1 was repeated with a lactic acid oligomer containing 16 lactyl i.e. —OCH(CH$_3$)CO— units. Approximately 1,437 gms of the oligomer at a temperature of 170° was fed over a 3 hour period at a rate of about 8 gms/min to the depolymerizer maintained at 210°. The vapor product stream from the depolymerizer was partially condensed as before at 132° and 10 mm Hg to yield a water-acid fraction (208 gms) and a crude liquid lactide condensate (733 gms) having an acidity content of 324 meq/kg. The residue in the depolymerizer amounted to 484 gms.

The crude lactide condensate was stored for 14 days at 0° and remelted by microwave heating. Its acidity was redetermined and found to have increased to 544 meq/kg.

721 gms of the crude lactide was then fractionally distilled at 30 mm Hg, a head temperature of 150°–155° and a reflux of 4:1 to 6:1. Five cuts were taken:

| Cut | Weight | Acidity |
|---|---|---|
| 1 | 41.8 | 2940 |
| 2 | 79.3 | 96 |
| 3 | 163.7 | 54 |
| 4 | 143.3 | 37 |
| 5 | 99.4 | 133 |
| Heel | 101.4 | 980 |

EXAMPLE 3

Fractions of previously refined (distilled) lactide having acidities of less than about 100 meq/kg were combined and melted to provide 1,017 gms having an initial acidity of 59 meq/kg, which increased to 75 meq/kg after storage overnite at 25° and then remelted at 100°.

1,013 gms of the lactide composition was fractionally distilled as described in Examples 4 and 5. the pressure was 30 mm Hg, the head temperature 134° to 156°, and the operating reflux ratio was about 4:1.

| Cut | Wt. gms | Acidity, meq/kg Initial | After 20 hrs at 25° |
|---|---|---|---|
| 1 | 79.6 | 484 | 513 |
| 2 | 90.6 | 18 | 21 |
| 3 | 104.6 | 1 | 9 |
| 4 | 95.6 | 2 | 10 |
| 5 | 110.2 | 3 | 8 |
| 6 | 108.4 | 0 | 3 |
| 7 | 110.3 | 5 | 8 |
| 8 | 107.9 | not. det. | 22 |
| 9 | 53.2 | not. det. | 22 |
| Heel | 117.8 | not. det. | 151 |

These results show that the invention process is capable of producing low acid content lactide even under batch distillation conditions. They also show that the acid-lactide system is a dynamic one with the acid content tending to increase an standing, even at ambient temperatures unless precautions are taken to exclude moisture.

The distillation results also suggest that low, substantially nil, acid content lactide and other dimeric cyclic esters at alpha-hydroxycarboxylic acids could be obtained in high yields under continuous distillation conditions, thereby completely obviating the need for solvent treatments to obtain such high quality polymer-grade material.

EXAMPLE 4

The procedure of Example 1 was carried out with 2 kg of 88% lactic acid containing 6 gms of stannous octoate, which was dehydrated and oligomerized by heating at 120° to 180° with removal of 407 gms of water. The resulting oligomer contained on the average 10 lactyl units. Approximately 1,437 gms of the molten (150°–160°) oligomer was fed at a rate of about 9.6 gms/min to the depolymerizer maintained at 220° C. and 10 mm Hg pressure. The vapor product stream issuing from the depolymerizer was partially condensed in the flash chamber at 100°–103° and 2 mm Hg pressure. The condensate, about 890 gms, contained 755 meq/kg of acidity.

The above condensate was batch distilled as described in Example 5. The pressure was 30 mm Hg, the head temperature ranged from an initial 117° to 135° and finally at 155° for a first cut and at 155° for 5 additional cuts, and the reflux ratio ranged from 12:1 to 1:1 for cuts 3–6. The 6 cuts were as follows:

| Cut | Wt. gms | Acidity, meq/kg |
|---|---|---|
| 1 | 104.4 | 2825 |
| 2 | 123.1 | 41 |
| 3 | 114.5 | 24 |
| 4 | 106.7 | 26 |
| 5 | 130.9 | 190 |
| 6 | 20.9 | 343 |

EXAMPLE 5

The procedure of Example 1 was repeated. The lactic acid oligomer contained 11.3 lactyl units. Approximately 1,437 gms of the molten (150°) oligomer was fed to the depolymerizer over a 165 minute period, and the vapor product stream from the depolymerizer was fed to the partial condensation chamber maintained at 100° and 2 mm Hg.

The overhead from the partial condenser, collected in two cold traps, weighed 69.7 gms, the crude lactide remaining in the condensing chamber weighed 1,351 gms and had 511 meq/kg of acidity.

The crude lactide was fractionally distilled batchwise as before, and 7 cuts were taken:

| Cut | Wt. gms | Acidity, meq/kg |
|---|---|---|
| 1 | 129.4 | 2529 |
| 2 | 161.5 | 230 |
| 3 | 175.6 | 36 |
| 4 | 145.8 | 24 |
| 5 | 168.9 | 21 |
| 6 | 153.0 | 19 |
| 7 | 79.7 | 35 |

Comparison of the batch distillation results of Examples 2, 4 and 5 obtained at 30 mm Hg with those of Example 1 obtained at 5 mm Hg shows that better results are obtained at the lower pressure. This can be attributed to a lesser tendency for the distillation mass to produce acidic species at the lower temperatures pertaining at the lower pressure.

EXAMPLE 6

Distillation cuts 2, 3, 4 and 5 from Example 4 were combined with distillation cuts 3, 4, 5, 6 and 7 from Example 5. 1167 gms of the composite having 59 meq/kg of acidity was batchwise fractionally distilled as in Example 1 except that the distillation pressure was 30 mm Hg, and the temperature was 155° at the head and 160°-163° at the base of the column. The reflux ratio was 4:1 throughout. Seven distillation cuts were taken:

| Cut | Wt. gms | Acidity, meq/kg |
|---|---|---|
| 1 | 162.1 | 236 |
| 2 | 131.3 | 5 |
| 3 | 130.3 | 17 |
| 4 | 165.7 | 14 |
| 5 | 152.2 | 9 |
| 6 | 177.1 | 12 |
| 7 | 62.9 | 14 |
| Heel | 135.1 | 1130 |

Having thus described and exemplified the invention with a certain degree of particularity, it should be appreciated that the following claims are not to be so limited but are to be afforded a scope commensurate with the wording of each element of the claim and equivalents thereof.

We claim:

1. A method for the separation of alpha hydroxyl dimeric cyclic ester from a vaporous effluent from the depolymerization of alpha hydroxylic oligomer containing water, minor amounts of hydroxycarboxylic acid, alpha hydroxyl dimeric cyclic ester and alpha hydroxylic oligomer without the addition of solvent by
   (1) partially condensing the vaporous effluent stream to remove water therefrom;
   (2) feeding the condensate through a feed inlet to an intermediate point within a continuous fractionation column operating at a temperature no higher than 220° C. to effect vaporization of the hydroxycarboxylic acid and the dimeric cyclic ester;
   (3) removing from the top of the column a first vapor stream containing a major amount of alpha hydroxylic carboxylic acid and condensing the first stream;
   (4) from a point below the condensate feed inlet removing a second vapor stream containing a major amount of dimeric cyclic ester and condensing the second stream; and
   (5) removing a liquid fraction from the lower end of the column containing a major amount of alpha hydroxylic oligomer.

2. The process of claim 1 wherein the depolymerizable oligomer is an oligomer of L-lactic acid and the lactide product is L-lactide.

3. The process of claim 2 wherein the distillation temperature is below about 200° C.

4. The process of claim 2 wherein the distillation is conducted below about 180° C.

5. A process for the separation and recovery of a dimeric cyclic ester from a vapor product stream containing said ester and minor amounts of one or more hydroxylic impurities including an alpha-hydroxycarboxylic acid more volatile than the cyclic ester, water and oligomeric hydroxycarboxylic acid higher-boiling than the cyclic ester, which process comprises condensing the vapor stream to form a dimeric cyclic ester condensate, fractionally distilling the resulting condensate and recovering a dimeric cyclic ester fraction having a substantially lowered content of water alpha-hydroxy acid, and oligomeric acid wherein the fractional distillation is conducted continuously and comprises the steps of:
   (a) providing a multi-stage distillation column having a feed inlet at a midpoint of the column, an overhead vapor takeoff at the upper end of the column, a vapor sidestream takeoff at a point below the midpoint feed inlet and a high-boiler take off at the lower end of the column;
   (b) feeding the cyclic ester condensate to the midpoint of the column;
   (c) establishing in the column (i) an overhead vapor fraction consisting essentially of water, when present, alpha-hydoxycarboxylic acid more volatile than the cyclic ester and little or no cyclic ester, (ii) a cyclic ester fraction below the midpoint feed inlet that is substantially free of water, lower-boiling acid and higher-boiling acid and (iii) a high-boiling fraction consisting largely of cyclic ester and higher-boiling oligomeric acids at the lower end of the column;
   (d) removing the overhead fraction from the upper end of the column;
   (e) removing the cyclic ester vapor fraction through the vapor sidestream takeoff; and
   (f) removing the higher-boiling fraction at the lower end of the column.

6. The process of claim 5 wherein the feed rate of the condensate to the column, the removal rate of the vapor overhead from the column, the removal rate of the cyclic ester fraction from the column and the removal rate of the high boiling fraction from the column are coordinated so as to establish a substantially steady state in the column.

7. The process of claim 5 wherein the cyclic ester is a lactide, the hydroxycarboxylic acid is lactic acid and the oligomeric hydroxy acid is an oligomer of lactic acid.

* * * * *